United States Patent
Timken (10) Patent No.: US 12,319,877 B2
(45) Date of Patent: *Jun. 3, 2025

(54) CIRCULAR ECONOMY FOR PLASTIC WASTE TO POLYPROPYLENE AND LUBRICATING OIL VIA REFINERY FCC AND ISOMERIZATION DEWAXING UNITS

(71) Applicant: Chevron U.S.A. Inc., San Ramon, CA (US)

(72) Inventor: Hye-Kyung Timken, Albany, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/636,100

(22) Filed: Apr. 15, 2024

(65) Prior Publication Data

US 2024/0255222 A1 Aug. 1, 2024

Related U.S. Application Data

(63) Continuation of application No. 18/051,002, filed on Oct. 30, 2022, now Pat. No. 11,959,025, which is a
(Continued)

(51) Int. Cl.
*C10G 1/10* (2006.01)
*B68G 15/00* (2006.01)
(Continued)

(52) U.S. Cl.
CPC .............. *C10G 1/10* (2013.01); *B68G 15/00* (2013.01); *C07C 4/06* (2013.01); *C08F 10/06* (2013.01);
(Continued)

(58) Field of Classification Search
CPC .......... C10G 1/10; C10G 1/002; C10G 11/18; C10G 45/58; C10G 2300/1003;
(Continued)

(56) References Cited

U.S. PATENT DOCUMENTS

| 3,845,157 A | 10/1974 | Woo et al. |
| 4,642,401 A | 2/1987 | Coenen et al. |

(Continued)

FOREIGN PATENT DOCUMENTS

| EP | 0 620 264 A2 | 10/1994 |
| JP | 9-48981 A | 2/1997 |

(Continued)

OTHER PUBLICATIONS

"The seven types of plastic", OpenLearn, pp. 1-9; Feb. 4, 2020, https://www.open.edu/openlearn/science-maths-technology/chemistry/the-seven-types-plastic.
(Continued)

*Primary Examiner* — Ellen M Mcavoy
(74) *Attorney, Agent, or Firm* — Merchant & Gould P.C.

(57) ABSTRACT

A continuous process for converting waste plastic into recycle for polypropylene polymerization is provided. The process integrates refinery operations to provide an effective and efficient recycle process. The process comprises selecting waste plastics containing polyethylene and polypropylene and then passing the waste plastics through a pyrolysis reactor to thermally crack at least a portion of the polyolefin waste and produce a pyrolyzed effluent. The pyrolyzed effluent is separated into offgas, a naphtha/diesel fraction, a heavy fraction, and char. The naphtha/diesel fraction is passed to a refinery FCC unit, from which is recovered a liquid petroleum gas $C_3$ olefin/paraffin mixture. The $C_3$ paraffins and $C_3$ olefins are separated into different fractions with a propane/propylene splitter. The $C_3$ olefin fraction is passed to a propylene polymerization reactor. The $C_3$ paraffin fraction is optionally passed to a dehydrogenation unit to produce additional propylene and then the resulting $C_3$ olefin is passed to a propylene polymerization reactor. The
(Continued)

Establishment of Circular Economy for Recycle of PP via Pyrolysis of PE/PP Waste Plastics Through Oil Refinery Operation heavy fraction of pyrolyzed oil is passed to an isomerization dewaxing unit to produce a lubricating base oil.

10 Claims, 3 Drawing Sheets

Related U.S. Application Data continuation of application No. 17/131,894, filed on Dec. 23, 2020, now Pat. No. 11,518,945.

(60) Provisional application No. 62/952,867, filed on Dec. 23, 2019.

(51) Int. Cl.
| | |
|---|---|
| *C07C 4/06* | (2006.01) |
| *C08F 10/06* | (2006.01) |
| *C10B 53/07* | (2006.01) |
| *C10G 1/00* | (2006.01) |
| *C10G 11/18* | (2006.01) |
| *C10G 45/58* | (2006.01) |
| *C10M 109/02* | (2006.01) |
| *C10M 177/00* | (2006.01) |
| *F26B 5/08* | (2006.01) |
| *F26B 11/02* | (2006.01) |
| *F26B 25/00* | (2006.01) |
| *C10N 70/00* | (2006.01) |

(52) U.S. Cl.
CPC .............. *C10B 53/07* (2013.01); *C10G 1/002* (2013.01); *C10G 11/18* (2013.01); *C10G 45/58* (2013.01); *C10M 109/02* (2013.01); *C10M 177/00* (2013.01); *F26B 5/08* (2013.01); *F26B 11/022* (2013.01); *F26B 25/003* (2013.01); *C10G 2300/1003* (2013.01); *C10G 2300/202* (2013.01); *C10G 2300/205* (2013.01); *C10G 2300/304* (2013.01); *C10G 2300/305* (2013.01); *C10G 2300/308* (2013.01); *C10G 2300/4006* (2013.01); *C10G 2300/4012* (2013.01); *C10G 2300/4018* (2013.01); *C10G 2400/02* (2013.01); *C10G 2400/04* (2013.01); *C10G 2400/08* (2013.01); *C10G 2400/10* (2013.01); *C10G 2400/26* (2013.01); *C10M 2203/003* (2013.01); *C10N 2070/00* (2013.01)

(58) Field of Classification Search
CPC ........... B68G 15/00; C07C 4/06; C08F 10/06; C10B 53/07; C10M 109/02; C10M 177/00; F26B 5/08; F26B 11/022; F26B 25/003
See application file for complete search history.

(56) References Cited

U.S. PATENT DOCUMENTS

| | | | |
|---|---|---|---|
| 5,849,964 | A | 12/1998 | Holighaus et al. |
| 5,981,818 | A | 11/1999 | Purvis |
| 6,143,940 | A | 11/2000 | Miller et al. |
| 6,150,577 | A | 11/2000 | Miller et al. |
| 6,288,296 | B1 | 9/2001 | Miller et al. |
| 6,774,272 | B2 | 8/2004 | Miller |
| 6,822,126 | B2 | 11/2004 | Miller |
| 7,834,226 | B2 | 11/2010 | Miller |
| 8,088,961 | B2 | 1/2012 | Miller |
| 8,404,912 | B1 | 3/2013 | Miller |
| 8,480,880 | B2 | 7/2013 | Miller |
| 8,696,994 | B2 | 4/2014 | Miller |
| 11,174,437 | B2 * | 11/2021 | Timken .................. C10G 55/02 |
| 11,518,945 | B2 * | 12/2022 | Timken .................. F26B 25/003 |
| 11,959,025 | B2 * | 4/2024 | Timken .................. C10G 11/18 |
| 2003/0019789 | A1 | 1/2003 | Kwak |
| 2003/0199717 | A1 | 10/2003 | Miller |
| 2006/0108260 | A1 | 5/2006 | Henry |
| 2007/0238912 | A1 | 10/2007 | Smith, Jr. |
| 2011/0089071 | A1 | 4/2011 | Srinakruang |
| 2011/0089081 | A1 | 4/2011 | Srinakruang |
| 2014/0228204 | A1 | 8/2014 | Narayanaswamy et al. |
| 2016/0264874 | A1 | 9/2016 | Narayanaswamy et al. |
| 2016/0264885 | A1 | 9/2016 | Narayanaswamy et al. |
| 2016/0362609 | A1 | 12/2016 | Ward et al. |
| 2019/0002369 | A1 | 1/2019 | Dries |
| 2019/0161683 | A1 | 5/2019 | Narayanaswamy et al. |
| 2019/0177626 | A1 | 6/2019 | Ramamurthy |
| 2019/0284476 | A1 | 9/2019 | Gaber et al. |
| 2019/0367428 | A1 | 12/2019 | Ramamurthy |
| 2021/0130699 | A1 | 5/2021 | Bitting |
| 2021/0189248 | A1 | 6/2021 | Timken |
| 2021/0189249 | A1 | 6/2021 | Timken |
| 2021/0189250 | A1 | 6/2021 | Timken |
| 2021/0189251 | A1 | 6/2021 | Timken |
| 2021/0189252 | A1 | 6/2021 | Timken |
| 2021/0189253 | A1 | 6/2021 | Timken |
| 2021/0189269 | A1 | 6/2021 | Timken |
| 2021/0332299 | A1 | 10/2021 | Timken |
| 2021/0332300 | A1 | 10/2021 | Timken |
| 2021/0348061 | A1 | 11/2021 | Daggupati |

FOREIGN PATENT DOCUMENTS

| | | |
|---|---|---|
| JP | 9-48982 A | 2/1997 |
| JP | 9-48983 A | 2/1997 |
| JP | 11-61147 A | 3/1999 |
| JP | 11-61148 A | 3/1999 |
| JP | 2003-528206 A | 9/2003 |
| JP | 2005-527672 A | 9/2005 |
| JP | 2011-508808 A | 3/2011 |
| JP | 2016-514170 A | 5/2016 |
| JP | 2019-534926 A | 12/2019 |
| WO | 2001/064760 A2 | 9/2001 |
| WO | 2016/059565 A2 | 4/2016 |

OTHER PUBLICATIONS

International Search Report and Written Opinion mailed Mar. 15, 2021 in PCT/US2020/066810.
Supplementary European Search Report issued Nov. 29, 2023 in EP 20906534.
Office Action issued in Japanese Patent Application No. 2022-538699, mailed Oct. 23, 2024.
Office Action issued in Japanese Patent Application No. 2022-538702, mailed Oct. 23, 2024.
Office Action issued in Japanese Patent Application No. 2022-538704, mailed Oct. 23, 2024.
Office Action issued in Japanese Patent Application No. 2022-538700, mailed Nov. 8, 2024.
Office Action issued in Japanese Patent Application No. 2022-538701, mailed Nov. 8, 2024.
Office Action issued in Japanese Patent Application No. 2022-538697, mailed Nov. 8, 2024.
Office Action issued in Japanese Patent Application No. 2022-538698, mailed Nov. 8, 2024.
Office Action issued in Japanese Patent Application No. 2022-538703, mailed Nov. 8, 2024.
Pall Corporation, Refineries: Application Focus, Oct. 1, 2018 (Oct. 1, 2018), XP093101978, Retrieved from the Internet: URL:https://www.pall.com/content/dam/pall/oil-gas/literature-library/non-gated/pdf/refinery-hf-alkylation.pdf.
Extended European Search Report issued in related European Patent Application No. 24200399.4, Nov. 25, 2024.

* cited by examiner

Figure 1 (base case)
Pyrolysis of Waste Plastics to Fuel or Wax

Figure 2

Establishment of Circular Economy for Recycle of PP via Pyrolysis of PE/PP Waste Plastics Through Oil Refinery Operation Figure 3
Plastic Type Classification for Waste Plastics Recycling

CIRCULAR ECONOMY FOR PLASTIC WASTE TO POLYPROPYLENE AND LUBRICATING OIL VIA REFINERY FCC AND ISOMERIZATION DEWAXING UNITS

CROSS REFERENCE TO RELATED APPLICATIONS

The present application is a continuation of U.S. patent application Ser. No. 18/051,002 filed Oct. 30, 2022, which is also a continuation of U.S. patent application Ser. No. 17/131,894 filed Dec. 23, 2020 (now U.S. Pat. No. 11,518, 945), which claims priority to U.S. Provisional Application No. 62/952,867 filed Dec. 23, 2019, the complete disclosures of which are incorporated herein by reference in their entireties.

BACKGROUND

The world has seen extremely rapid growth of plastics production. According to PlasticsEurope Market Research Group, the world plastics production was 335 million tons in 2016, 348 million tons in 2017 and 359 million tons in 2018. According to Mckinsey & Company, the global plastics-waste volume was estimated about 260 million tons per year in 2016, and projected to be 460 million tons per year by 2030 if the current trajectory continues.

Single use plastic waste has become an increasingly important environmental issue. At the moment, there appear to be few options for recycling polyethylene and polypropylene waste plastics to value-added chemical and fuel products. Currently, only a small amount of polyethylene and polypropylene is recycled via chemical recycling, where recycled and cleaned polymer pellets are pyrolyzed in a pyrolysis unit to make fuels (naphtha, diesel), stream cracker feed or slack wax.

Processes are known which convert waste plastic into hydrocarbon lubricants. For example, U.S. Pat. No. 3,845, 157 discloses cracking of waste or virgin polyolefins to form gaseous products such as ethylene/olefin copolymers which are further processed to produce synthetic hydrocarbon lubricants. U.S. Pat. No. 4,642,401 discloses the production of liquid hydrocarbons by heating pulverized polyolefin waste at temperatures of 150-500° C. and pressures of 20-300 bars. U.S. Pat. No. 5,849,964 discloses a process in which waste plastic materials are depolymerized into a volatile phase and a liquid phase. The volatile phase is separated into a gaseous phase and a condensate. The liquid phase, the condensate and the gaseous phase are refined into liquid fuel components using standard refining techniques. U.S. Pat. No. 6,143,940 discloses a procedure for converting waste plastics into heavy wax compositions. U.S. Pat. No. 6,150,577 discloses a process of converting waste plastics into lubricating oils. EP0620264 discloses a process for producing lubricating oils from waste or virgin polyolefins by thermally cracking the waste in a fluidized bed to form a waxy product, optionally using a hydrotreatment, then catalytically isomerizing and fractionating to recover a lubricating oil.

Other documents which relate to processes for converting waste plastic into lubricating oils include U.S. Pat. Nos. 6,288,296; 6,774,272; 6,822,126; 7,834,226; 8,088,961; 8,404,912 and 8,696,994; and U.S. Patent Publication Nos. 2019/0161683; 2016/0362609; and 2016/0264885. The foregoing patent documents are incorporated herein by reference in their entirety.

The current method of chemical recycling via pyrolysis cannot make a big impact for the plastics industry. The current pyrolysis operation produces poor quality fuel components (naphtha and diesel range products), but the quantity is small enough that these products can be blended into fuel supplies. However, this simple blending cannot continue if very large volumes of waste polyethylene and polypropylene are to be recycled to address environmental issues. The products as produced from a pyrolysis unit are of too poor quality to be blended in large amounts (for example 5-20 vol. % blending) in transportation fuels.

In order to achieve recycling of single use plastics in an industrially significant quantity to reduce its environmental impact, more robust processes are needed. The improved processes should establish "circular economy" for the waste polyethylene and polypropylene plastics where the spent waste plastics are recycled effectively back as starting materials for polymers and high value byproducts.

SUMMARY

Provided is a continuous process for converting waste plastic. The waste plastic is recycled for polypropylene polymerization. The process comprises first selecting waste plastics containing polyethylene and/or polypropylene. These waste plastics are then passed through a pyrolysis reactor to thermally crack at least a portion of the polyolefin waste and produce a pyrolyzed effluent. The pyrolyzed effluent is separated into offgas, a naphtha/diesel fraction, a heavy fraction, and char.

The incorporation of the process with an oil refinery is an important aspect of the present process, and allows the creation of a circular economy with a single use waste plastic such as polypropylene. Thus, the separated naphtha/diesel fraction is passed to a refinery FCC unit, from which a liquid petroleum gas $C_3$ olefin/paraffin mixture is recovered. In the present process, the $C_3$ paraffin and $C_3$ olefin are separated into different fractions. The $C_3$ olefin is passed to a propylene polymerization reactor to produce polypropylene. Optionally, the $C_3$ paraffin is passed to a dehydrogenation unit to produce additional propylene. The heavy fraction can be passed to an isomerization dewaxing unit to produce a base oil.

The refinery will generally have its own hydrocarbon feed flowing through the refinery units. The flow volume of naphtha/diesel or a waxy heavy fraction generated from the pyrolysis of waste plastic to the refinery units can comprise any practical or accommodating volume % of the total flow to the refinery units. Generally, the flow of fractions generated from the waste plastic pyrolysis, for practical reasons, can be up to about 50 vol. % of the total flow, i.e., the refinery flow and the fraction flow. In one embodiment, the flow of the naphtha/diesel is an amount up to about 20 vol. % of the total flow.

Among other factors, it has been found that by adding refinery operations one can upgrade the waste pyrolysis oil or wax to a higher value product such as gasoline, jet, diesel, and base oil. But also, by adding refinery operations it has been found that clean propane and propylene can be efficiently and effectively produced from the waste pyrolysis and for ultimate polypropylene polymer production. Positive economics are realized for the overall process from recycled plastics to a polypropylene product with product quality identical to that of virgin polymer.

DETAILED DESCRIPTION

In the present process, provided is a method to recycle waste polyethylene and/or polypropylene back to virgin polypropylene to establish a circular economy by combining distinct industrial processes. A substantial portion of polyethylene and polypropylene polymers are used in single use plastics and get discarded after its use. The single use plastic waste has become an increasingly important environmental issue. At the moment, there appear to be few options for recycling polyethylene and polypropylene waste plastics to value-added chemicals and fuel products. Currently, only a small amount of polyethylene/polypropylene is recycled via chemical recycling, where recycled and cleaned polymer pellets are pyrolyzed in a pyrolysis unit to make fuels (naphtha, diesel), steam cracker feed or slack wax.

Polypropylene is used widely in various consumer and industrial products. Polypropylene is the second-most widely produced commodity plastic after polyethylene with its mechanical ruggedness and high chemical resistance. Polypropylene is widely used in packaging, film, fibers for carpets and clothing, molded articles and extruded pipes. Today, only a small portion of spent polypropylene products is collected for recycling, due to the inefficiencies and ineffectiveness of the recycling efforts discussed above.

Figure 1:
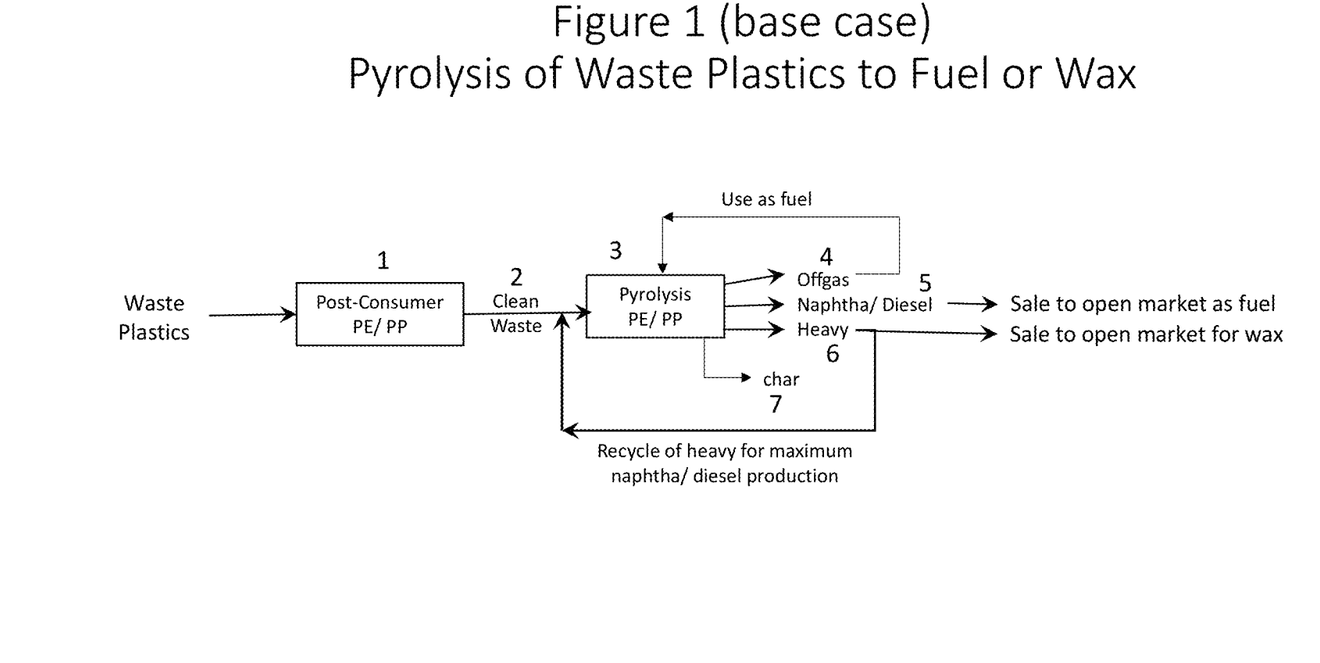
FIG. 1 depicts the current practice of pyrolyzing waste plastics to produce fuel or wax (base case).

FIG. 1 shows a diagram of pyrolysis of waste plastics fuel or wax that is generally operated in the industry today. As noted above, generally, polyethylene and polypropylene wastes are sorted together 1. The cleaned polyethylene/polypropylene waste 2 is converted in a pyrolysis unit 3 to offgas 4 and pyrolysis oil (liquid product). The offgas 4 from the pyrolysis unit is used as fuel to operate the pyrolysis unit 3. An on-site distillation unit (not shown) separates the pyrolysis oil to produce naphtha and diesel 5 products which are sold to fuel markets. The heavy pyrolysis oil fraction 6 is recycled back to the pyrolysis unit 3 to maximize the fuel yield. Char 7 is removed from the pyrolysis unit 3. The heavy fraction 6 is rich in long chain, linear hydrocarbons, and is very waxy (i.e., forms paraffinic wax upon cooling to ambient temperature). Wax can be separated from the heavy fraction 6 and sold to the wax markets.

The present process converts pyrolyzed polypropylene and/or polyethylene waste plastic in large quantities by integrating the waste polymer pyrolysis product streams into an oil refinery operation. The resulting processes produce the feedstocks for the polymers (liquid petroleum gas (LPG) propane stream for a propane dehydrogenation unit and propylene for propylene polymerization unit), as well as high quality gasoline and diesel fuel, and/or quality base oil.

Generally, the present process provides a circular economy for polypropylene plants. Polypropylene is produced via polymerization of pure propylene. Clean propylene can be made from a propane dehydrogenation unit. Also, propylene can be obtained from an oil refinery fluid catalytic cracking (FCC) unit, which produces a mix of propylene and propane liquefied petroleum gas (LPG). Pure propylene is separated from the mix using a propane/propylene splitter, a high efficiency distillation column (PP splitter).

By adding refinery operations to upgrade the waste pyrolysis oil and wax to higher value products (gasoline, diesel, and base oil) and to produce clean propane and propylene for ultimate polypropylene polymer production, positive economics are realized for the overall processes from recycled plastics to polypropylene product with product quality identical to that of the virgin polymer.

A pyrolysis unit produces poor quality products containing contaminants, such as calcium, magnesium, chlorides, nitrogen, sulfur, dienes, heavy components, which products cannot be used in large quantity for blending in transportation fuels. It has been discovered that by having these products go through the refinery units, the contaminants can be captured in pre-treating units and their negative impacts diminished. The fuel components can be further upgraded with appropriate refinery units with chemical conversion processes, with the final transportation fuels produced by the integrated process being of higher quality and meeting the fuels quality requirements. The present process will upgrade the wax into valuable base oil. The integrated process will generate a much cleaner and more pure propane stream for the propane dehydrogenation unit and ultimately for polypropylene production. These large on-spec productions allow "cyclical economy" for the recycle plastics to be feasible.

The carbon in and out of the refinery operations are "transparent," meaning that all the molecules from the waste plastic do not necessarily end up in the exact olefin product cycled back to the polyolefin plants, but are nevertheless assumed as "credit" as the net "green" carbon in and out of the refinery is positive. With these integrated processes, the amount of virgin feeds needed for polypropylene plants will be reduced significantly.

Figure 2:
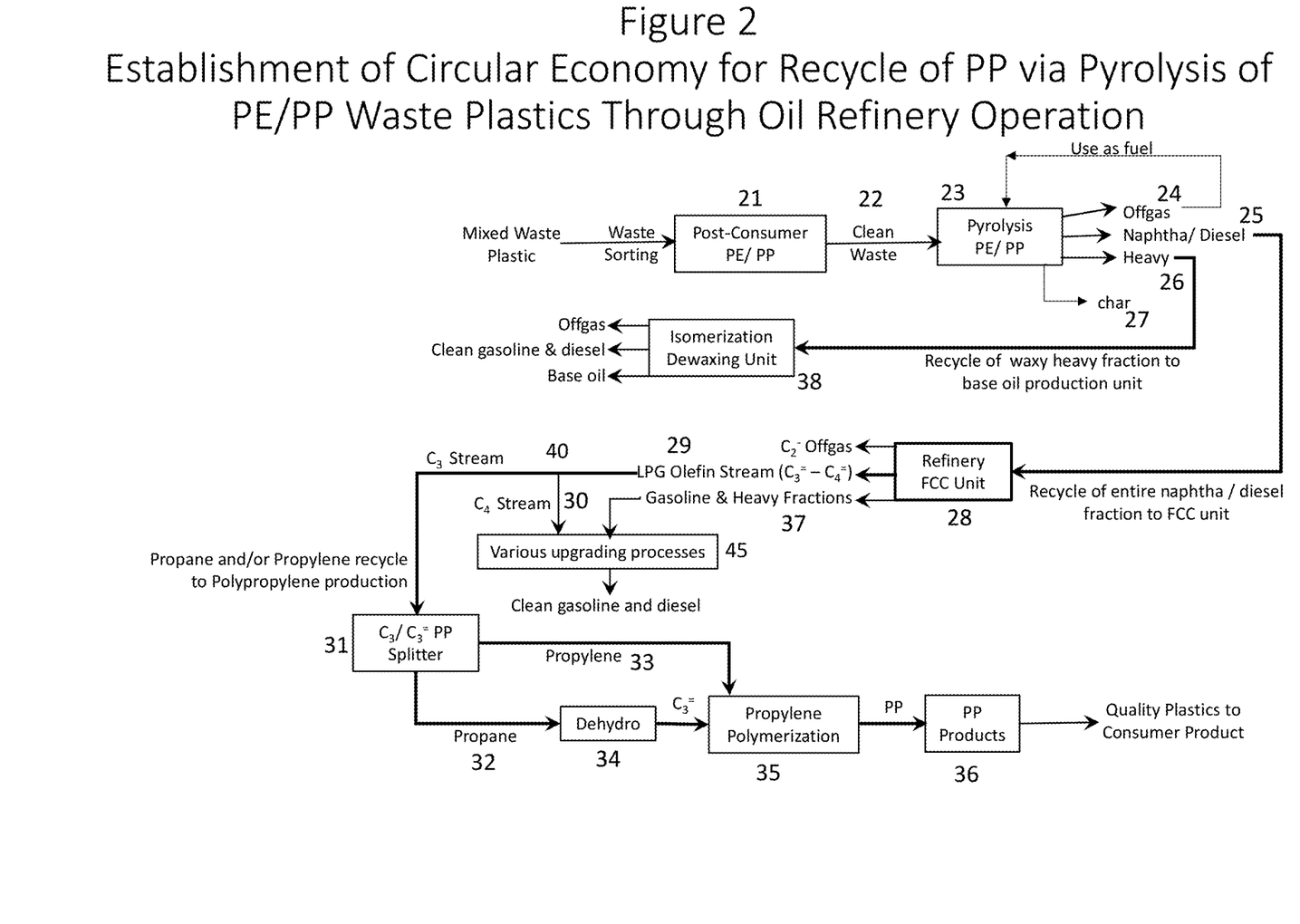
FIG. 2 depicts a present process for establishing a circular economy for waste plastics.

FIG. 2 shows the present integrated process, integrating refinery operations with recycle for effective polypropylene production. In FIG. 2, mixed waste plastics are sorted together 21. The cleaned waste plastic 22 is converted in a pyrolysis unit 23 to offgas 24 and a pyrolysis oil (liquid product) and optionally wax (solid product at ambient temperature). The offgas 24 from the pyrolysis unit can be used as fuel to operate the pyrolysis unit 23. The pyrolysis oil is separated, generally by an on-site distillation unit, into a naphtha/diesel fraction 25, and a heavy faction 26. Char 27 is removed from the pyrolysis unit 23 after completion of the pyrolysis step.

The pyrolysis unit can be located near the waste plastics collection site, which site could be away from a refinery, near a refinery, or within a refinery. When the pyrolysis unit is located away from the refinery, the pyrolysis oil (naphtha/diesel and heavies) and wax can be transferred to the refinery by truck, barge, rail car, or pipeline. It is preferred, however, that the pyrolysis unit is within the plastics collection site or within the refinery.

Figure 3:
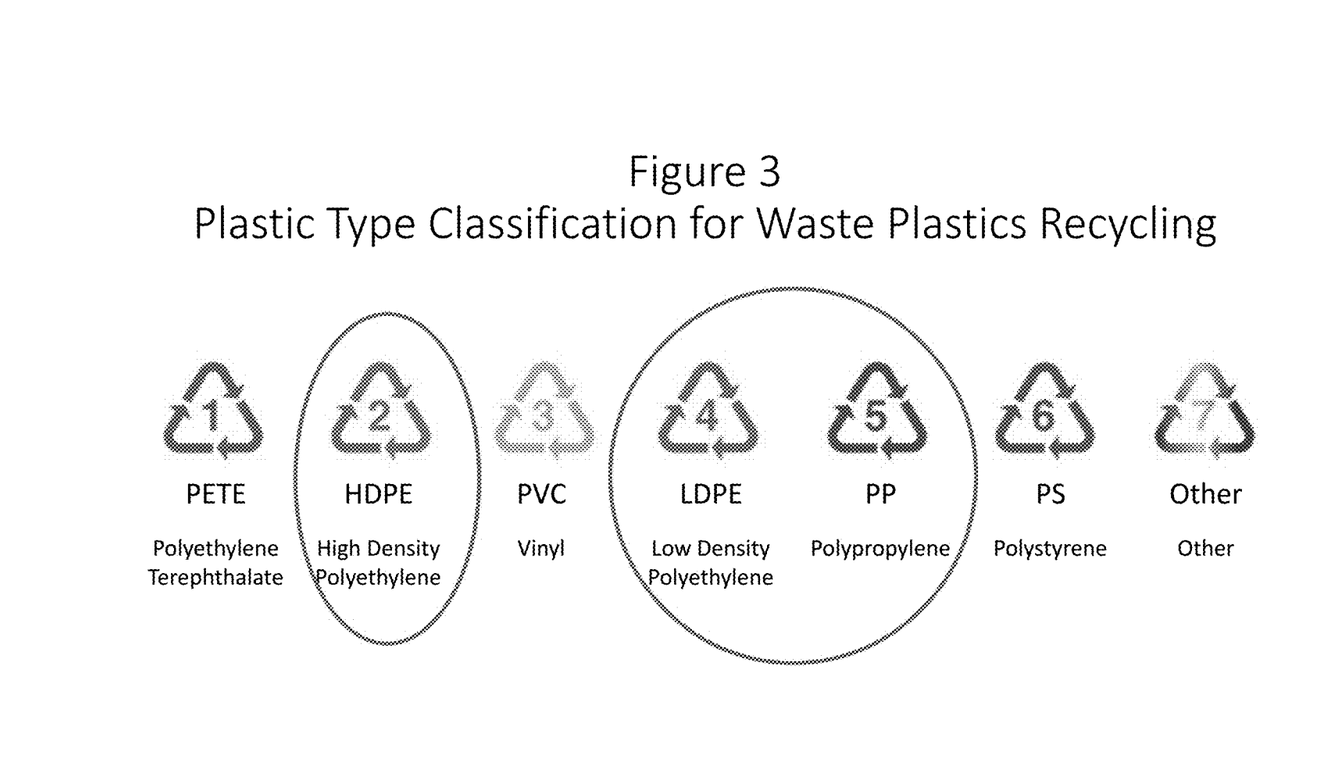
FIG. 3 depicts the plastic type classification for waste plastics recycling.

The preferred starting material for the present process is sorted waste plastics containing predominantly polyethylene and polypropylene (plastics recycle classification types 2, 4, and 5). The pre-sorted waste plastics are washed and shredded or pelleted to feed to a pyrolysis unit for thermal cracking. FIG. 3 depicts the plastic type classification for waste plastics recycling. Classification types 2, 4, and 5 are high density polyethylene, low density polyethylene and polypropylene, respectively. Any combination of the polyethylene and polypropylene waste plastics can be used. For the present process, at least some polypropylene waste plastic is preferred.

Proper sorting of waste plastics is very important in order to minimize contaminants such as N, Cl, and S. Plastics waste containing polyethylene terephthalate (plastics recycle classification type 1), polyvinyl chloride (plastics recycle classification type 3) and other polymers (plastics recycle classification type 7) need to be sorted out to less than 5%, preferably less than 1% and most preferably less than 0.1%. The present process can tolerate a moderate amount of polystyrene (plastics recycle classification type 6). Waste polystyrene needs to be sorted out to less than 30%, preferably less than 20% and most preferably less than 5%.

Washing of waste plastics removes metal contaminants such as sodium, calcium, magnesium, aluminum, and non-metal contaminants coming from other waste sources. Non-metal contaminants include contaminants coming from the Periodic Table Group IV, such as silica, contaminants from Group V, such as phosphorus and nitrogen compounds, contaminants from Group VI, such as sulfur compounds, and halide contaminants from Group VII, such as fluoride, chloride, and iodide. The residual metals, non-metal contaminants, and halides need to be removed to less than 50 ppm, preferentially less than 30 ppm and most preferentially to less than 5 ppm.

If the washing does not remove the metals, non-metal contaminants, and halides impurities adequately, then a separate guard bed can be used to remove the metals and non-metal contaminants.

The pyrolyzing is carried out by contacting a plastic material feedstock in a pyrolysis zone at pyrolysis conditions, where at least a portion of the feed(s) is cracked, thus forming a pyrolysis zone effluent comprising 1-olefins and n-paraffins. Pyrolysis conditions include a temperature of from about 400° C. to about 700° C., preferably from about 450° C. to about 650° C. Conventional pyrolysis technology teaches operating conditions of above-atmospheric pressures. See e.g., U.S. Pat. No. 4,642,401. Additionally, it has been discovered that by adjusting the pressure downward, the yield of a desired product can be controlled. See, e.g., U.S. Pat. No. 6,150,577. Accordingly, in some embodiments where such control is desired, the pyrolysis pressure is sub-atmospheric.

FIG. 2 shows the present integrated process where only the naphtha/diesel fraction from the pyrolysis is sent to an FCC unit 28. The naphtha/diesel fraction is fed either to the FCC reactor or to the distillation column depending on the feed quality. The fluid catalytic cracking (FCC) process is widely used in the refining industry for conversion of atmospheric gas oil, vacuum gas oil, atmospheric residues and heavy stocks recovered from other refinery operations into high-octane gasoline, light fuel oil, heavy fuel oil, olefin-rich light gas (LPG) and coke. FCC uses a high activity zeolite catalyst to crack the heavy hydrocarbon molecules at a 950-990° F. reactor temperature in a riser with a short contact time of a few minutes or less. LPG streams containing olefins (propylene, butylene) are commonly upgraded to make alkylate gasoline, or to be used in chemicals manufacturing. A conventional FCC unit is used.

The refinery will generally have its own hydrocarbon feed flowing through the refinery units. The flow volume of naphtha/diesel generated from the pyrolysis of waste plastic to the refinery units, here an FCC unit, can comprise any practical or accommodating volume % of the total flow to the refinery units. Generally, the flow of the naphtha/diesel fraction generated from the waste plastic pyrolysis, for practical reasons, can be up to about 50 vol. % of the total flow, i.e., the refinery flow and the naphtha/diesel flow. In one embodiment, the flow of the naphtha/diesel is an amount up to about 20 vol. % of the total flow. In another embodiment, the flow of the naphtha/diesel is an amount up to about 10 vol. % of the total flow. About 20 vol. % has been found to be an amount that is quite practical in its impact on the refinery while also providing excellent results and being an amount that can be accommodated. The amount of naphtha/diesel generated from the pyrolysis can of course be controlled so that the fraction passed to the refinery units provides the desired volume % of the flow. Flow of the heavy fraction to the dewaxing unit can similarly be controlled and/or adjusted.

The FCC unit 28 produces a liquefied petroleum gas olefin streams 29 comprising $C_3^=/C_3$ olefin/paraffin mix and $C_4^=/C_4$ olefin/paraffin mix. The $C_3$ olefin/paraffin mix is recovered at 40, then the propane and propylene stream is split by a PP splitter 31 to produce pure streams of propane 32 and propylene 33. The propylene stream 33 can be fed directly to the polypropylene unit 35 to produce polypropylene resin. Polypropylene consumer products can then be made 36.

The pure propane 32 can be fed to a propane dehydrogenation unit 34 to make additional propylene, and then ultimately polypropylene in a propylene polymerization unit 35.

Dehydrogenation of propane is practiced widely in the industry to produce propylene. The reaction is endothermic, conversion is maintained by multi-stage reactors and inter-stage heaters. The unit typically operates at high temperature (>900° F.) and low pressure (<50 psig) in the presence of noble metal (Pt) catalyst. The multi-stage process generates approximately 85% purity propylene/propane mixture. This stream is directed to a propane/propylene (PP) splitter which is a high efficiency distillation column. The splitter produces pure propylene stream with 99.5-99.8% purity.

The PP splitter unit and/or propane dehydrogenation unit can be located away from a refinery, near a refinery, or within a refinery. The propane/propylene mix is sent to the PP splitter by truck, barge, rail car or pipeline. It is preferred that the PP splitter unit and propane dehydrogenation unit are close proximity of a refinery FCC unit.

Polypropylene is produced via chain-growth polymerization from the monomer propylene. A Ziegler-Natta catalyst or metallocene catalyst is used to catalyze the polymerization of propylene to polypropylene polymer with desired properties. These catalysts are activated with special cocatalyst containing an organoaluminum compounds. The industrial polymerization processes uses either gas phase polymerization in a fluidized bed reactor or bulk polymerization in loop reactors. The gas phase polymerization typically runs at 50-90° C. temperature and a pressure of 8-35 atm in the presence of $H_2$. The bulk polymerization proceeds at 60 to 80° C. and 30-40 atm pressure is applied to keep the propylene in liquid state.

The propylene polymerization unit is preferably located near the refinery so that the feedstock (propylene) can be transferred via pipeline. For a petrochemical plant located away from the refinery, the feedstock can be delivered via truck, barge, rail car or pipeline.

The $C_4$ 30 and heavy hydrocarbon product 37 from the FCC unit can be sent to appropriate refinery units 45 for upgrading into clean gasoline, diesel, or jet fuel.

The heavy, waxy pyrolysis oils or wax 26 from the pyrolysis unit 23 can be sent to a base oil dewaxing unit, generally an isomerization dewaxing unit 38 with a precious metal containing zeolite catalyst for hydroisomerization to produce lubricating base oil with excellent viscosity index and pour point. The flow of the heavy, waxy fraction can be controlled and adjusted as needed based upon the amount desired to be accommodated.

The isomerization dewaxing unit converts paraffinic, waxy heavy hydrocarbon material, typically boiling about 650° F., to high viscosity index (VI) lube oils. The unit typically consists of a feed hydrotreating section, isomerization dewaxing section, and distillation section.

The feed to the dewaxing unit is preferably subjected first to hydrogenation in a hydrotreating step. The hydrotreating occurs as part of the dewaxing unit. The feed hydrotreating step removes a significant portion of any nitrogen-containing, sulfur-containing, and/or oxygen-containing contaminants. The hydrotreating step also saturates a portion of olefins, dienes, and aromatics to improve the quality of the feed to the dewaxing unit. Typical hydrotreating conditions which are employed to remove contaminants while avoiding cracking include temperatures ranging from about 190° C. (374° F.) to about 340° C. (644° F.), pressure ranging from about 400 psig to about 3000 psig, space velocities (LHSV) in the range of about 0.1 $hr^{-1}$ to about 20 $hr^{-1}$, and hydrogen recycle rates ranging from about 400 to about 15,000 SCF/B. Hydrotreating catalysts include those conventionally used in hydrotreating units, containing metals such as Ni, Mo, Co, W and porous supports such as alumina, silica, or silica-alumina.

The hydrotreated heavy hydrocarbon is sent to the dewaxing reactor with an isomerization dewaxing catalyst which contains noble metal, intermediate pore size molecular sieve and binder. The catalyst preferably contains an intermediate pore size (10-membered ring) molecular sieve such as ZSM-23, ZSM-35, ZSM-48, ZSM-5, SSZ-32, SSZ-91, SAPO-11, SAPO-31 and SAPO-41. The noble metal includes Group VIII metals, such as Pt, Pd or mixture of Pt and Pd. Typically, porous alumina or silica is used to bind the material to produce catalyst pellets for the fixed bed reactor. Typical reaction conditions for the dewaxing reactor include temperature range of 200° C. (392° F.) to about 475° C. (887° F.), pressure ranging from about 200 psig to about 3000 psig, space velocities (LHSV) in the range of about 0.2 $hr^{-1}$ to about 10 $hr^{-1}$, and hydrogen recycle rates ranging from about 400 to about 15,000 SCF/B. The isomerization dewaxing catalyst converts n-paraffins to iso-paraffins, thereby reducing the pour point of the resulting oils and to form a high VI lube oil.

The effluent hydrocarbon from the isomerization dewaxing section is sent to a distillation unit to separate the effluent into various oil fractions, e.g., a base oil fraction that boils above ~650° F., a diesel fraction that boils about 300-700° F., and a gasoline fraction that boils about 80-400° F. The boiling points for the gasoline, jet and diesel fractions will be adjusted depending on the season and local specifications.

The benefits of a circular economy and an effective and efficient recycling campaign are realized by the present integrated process.

The following examples are provided to further illustrate the present process and its benefits. The examples are meant to be illustrative and not limiting.

Example 1: Properties of Pyrolysis Oil and Wax from Commercial Sources

Pyrolysis oil and wax samples were obtained from commercial sources and their properties are summarized in Table 1. These pyrolysis samples were prepared from waste plastics containing mostly polyethylene and polypropylene via thermal decomposition in a pyrolysis reactor at around 400-600° C., near atmospheric pressure without any added gas or a catalyst. A pyrolysis unit typically produces gas, liquid oil product, optionally wax product, and char. The pyrolysis unit's overhead gas stream containing thermally cracked hydrocarbon was cooled to collect condensate as pyrolysis oil (liquid at ambient temperature) and/or pyrolysis wax (solid at ambient temperature). The pyrolysis oil is the main product of the pyrolysis units. Some units produce pyrolysis wax as a separate product in addition to the pyrolysis oil.

TABLE 1

Properties of As-Received Oil and Wax from Pyrolysis of Waste Plastics

| | Pyrolysis Oil Sample A | Pyrolysis Oil Sample B | Pyrolysis Oil Sample C | Pyrolysis Oil Sample D | Pyrolysis Wax Sample E |
|---|---|---|---|---|---|
| Specific Gravity at 60° F. | 0.814 | 0.820 | 0.774 | — | 0.828 |
| Simulated Distillation, ° F. | | | | | |
| 0.5% (Initial Boiling Point) | 87 | 299 | 18 | 86 | 325 |
| 5% | 179 | 306 | 129 | 154 | 475 |
| 10% | 214 | 309 | 156 | 210 | 545 |
| 30% | 322 | 346 | 285 | 304 | 656 |
| 50% | 421 | 447 | 392 | 421 | 733 |
| 70% | 545 | 585 | 517 | 532 | 798 |
| 90% | 696 | 798 | 663 | 676 | 894 |
| 95% | 772 | 883 | 735 | 743 | 939 |
| 99.5% (Final Boiling Point) | 942 | 1079 | 951 | 888 | 1064 |
| Carlo-Erba Hydrocarbon Analysis | | | | | |
| Carbon, wt % | 87.6 | 84.21 | 85.46 | 85.97 | 85.94 |
| Hydrogen, wt % | 12.7 | 12.25 | 14.1 | 14.0 | 14.15 |
| Sum of C + H, wt % | 100.3 | 96.46 | 99.5 | 100.0 | 100.1 |
| H/C Molar Ratio | 1.73 | 1.75 | 1.98 | 1.96 | 1.98 |
| Bromine Number, g/100 g | 49 | 60 | 40 | 44 | 14 |
| Hydrocarbon Type | | | | | |
| Total Aromatics, vol % | 23.3 | 22.8 | 5.1 | 8.7 | 13.3 |
| Total Olefins & Naphthenes, vol % | 39.0 | 50.2 | 42.4 | 38.2 | 42.1 |
| Total Paraffins, vol % | 37.7 | 27 | 52.5 | 53.1 | 44.6 |
| Contaminants | | | | | |
| Total S, ppm | 48 | 29 | 7.8 | 99 | 6.3 |
| Total N, ppm | 751 | 1410 | 318 | 353 | 237 |

TABLE 1-continued

Properties of As-Received Oil and Wax from Pyrolysis of Waste Plastics

|  | Pyrolysis Oil Sample A | Pyrolysis Oil Sample B | Pyrolysis Oil Sample C | Pyrolysis Oil Sample D | Pyrolysis Wax Sample E |
|---|---|---|---|---|---|
| Total Cl, ppm | 113 | 62 | 41 | 70 | 4.7 |
| O in naphtha & distillate, ppm | 250 | — | 574 | — | — |
| Trace Elemental Impurities |  |  |  |  |  |
| Al, ppm | <1.1 | <0.56 | 0.6 | <0.53 | <0.68 |
| Ca, ppm | 1.4 | 11.5 | <0.5 | <0.53 | <0.68 |
| Fe, ppm | 4.9 | 11.9 | 1.6 | <1.1 | 3.1 |
| Mg, ppm | <0.51 | 1.3 | <0.52 | <0.53 | <0.68 |
| Na, ppm | 2.5 | <0.54 | <1.1 | <2.2 | <2.7 |
| Ni, ppm | <0.51 | <0.54 | <0.52 | 2 | <0.68 |
| V, ppm | <0.51 | <0.54 | <0.52 | 4 | <0.68 |
| P, ppm | 8.2 | 9.9 | <1.6 | <2.2 | 20.2 |
| Si, ppm | 82.5 | 49.6 | 13 | 17 | 3.1 |

ASTM D4052 method was used for specific gravity measurements. Simulated boiling point distribution curve was obtained using ASTM D2887 method. Carlo-Erba analysis for carbon and hydrogen was based on ASTM D5291 method. Bromine number measurement was based on ASTM D1159 method. Hydrocarbon-type analysis was done using a high resolution magnetic mass spectrometer using the magnet scanned from 40 to 500 Daltons. Total sulfur was determined using XRF per ASTM D2622 method. The nitrogen was determined using a modified ASTM D5762 method using chemiluminescence detection. The total chloride content was measured using combustion ion chromatography instrument using modified ASTM 7359 method. The oxygen content in naphtha and distillate boiling range was estimated using GC by GC/MS measurements with electron ionization detector for m/Z range of 29-500. Trace metal and non-metal elements in oil were determined using inductively coupled plasma-atomic emission spectrometry (ICP-AES).

Industrial pyrolysis process of sorted plastics, sourced predominantly from polyethylene and polypropylene waste, produced quality hydrocarbon streams with specific gravity ranging 0.7 to 0.9, and a boiling range from 18 to 1100° F. as in pyrolysis oil or pyrolysis wax.

The pyrolysis product is rather pure hydrocarbon made of mostly carbon and hydrogen. The hydrogen to carbon molar ratio varies from 1.7 to near 2.0. The Bromine Number is in the range of 14 through 60 indicating varying degrees of unsaturation coming from olefins and aromatics. The aromatic content is in the range of 5 to 23 volume % with a higher severity unit producing more aromatics. Depending on the process conditions of the pyrolysis unit, the pyrolysis products show paraffinic content ranging from mid-20 vol. % to mid-50 vol. %. The pyrolysis product contains a substantial amount of olefins. Samples A and B, pyrolysis oil produced under more severe conditions such as higher pyrolysis temperature and/or longer residence time, contain higher aromatic and lower paraffinic components, resulting H/C molar ratio of around 1.7 and high Bromine Number of 50-60. Samples C and D were produced at less severe conditions, and the pyrolysis oils are more paraffinic, resulting H/C molar ratio of close to 2.0 and Bromine Number around 40. Sample E, pyrolysis wax, is mostly paraffinic, saturated hydrocarbon with a substantial amount of normal hydrocarbons (as opposed to branched hydrocarbons) with low Bromine Number of only 14.

The following Examples 2 through 5 show the evaluation of waste plastics pyrolysis oil for transportation fuel.

Example 2: Fractionation of Pyrolysis Oil for Evaluation as Transportation Fuel

Sample D was distilled to produce hydrocarbon cuts representing gasoline (350° F.), jet (350-572° F.), diesel (572-700° F.) and the heavy (700° F.$^+$) fractions. Table 2 summarizes the boiling point distribution and impurity distributions among the distilled product fractions.

TABLE 2

Distillation of Pyrolysis Oil into Fuel Fractions

| Sample ID | Sample D | Sample F | Sample G | Sample H | Sample I |
|---|---|---|---|---|---|
| Intended Fraction |  | Gasoline Cut | Jet Cut | Diesel Cut | Unconverted |
| Cut Point Target, ° F. |  | 350⁻ | 350-572 | 572-700 | 700⁺ |
| Distillation Actual Yields, wt % |  | 37.2 | 38.0 | 15.0 | 9.3 |
| Simulated Distillation, F |  |  |  |  |  |
| IBP (0.5 wt %) | 86 | 27 | 299 | 539 | 640 |
| 5 wt % | 154 | 98 | 345 | 557 | 684 |
| 10 wt % | 210 | 147 | 365 | 574 | 696 |
| 30 wt % | 304 | 222 | 416 | 597 | 727 |
| 50 wt % | 421 | 270 | 457 | 619 | 758 |
| 70 wt % | 532 | 291 | 492 | 644 | 808 |
| 90 wt % | 676 | 337 | 546 | 674 | 898 |
| 95 wt % | 743 | 347 | 554 | 683 | 953 |
| FBP (99.5 wt %) | 888 | 385 | 591 | 711 | 1140 |
| Total S, ppm | 99 | 52 | 35 | 80 | 320 |
| Total N, ppm | 353 | 215 | 556 | 232 | 467 |
| Total Cl, ppm | 70 | 181 | 27 | 12 | 13 |

Example 3: Evaluation of Pyrolysis Oil Cut for Gasoline Fuel

Sample F, a pyrolysis oil cut for gasoline fuel boiling range, was evaluated to assess its potential to use as gasoline fuel. Sample F has the carbon number range of C5-C12, typical of the gasoline fuel.

Due to the olefinic nature of the pyrolysis oil, oxidation stability (ASTM D525) and gum forming tendency (ASTM D381) were identified as the most critical properties to examine. Research octane number (RON) and motor octane number (MON) are also the critical properties for engine performance. The RON and MON values were estimated from detailed hydrocarbon GC analysis.

TABLE 3

Evaluation of Pyrolysis Oil Naphtha Fraction for Gasoline Fuel

|  | Oxidation Stability, min | Washed Gum, mg/100 mL | RON | MON |
|---|---|---|---|---|
| Sample F | 90 | 5.0 | 71.4 | 67.7 |
| Reference gasoline | >1440 | 1 | 95.8 | 86.2 |
| 4/96 vol. % Blend of Sample F with reference gasoline | >1440 | 2.0 | 94.5 | 85.1 |
| 15/85 vol. % Blend of Sample F with reference gasoline | >1440 | 2.2 | 91.8 | 83.1 |

Sample F, a pyrolysis oil cut for gasoline fuel boiling range, cannot be used by itself as automotive gasoline fuel due to its poor quality. The gasoline fraction from the pyrolysis oil showed very poor oxidation stability in that Sample F failed only after 90 min compared to the target stability of longer than 1440 minutes. The pyrolysis gasoline exceeded the wash gum target of 4 mg/100 mL suggesting severe gum forming tendency. The pyrolysis gasoline has poor octane numbers compared to the reference gasoline. A premium unleaded gasoline was used as the reference gasoline.

We also examined the potential of blending of the pyrolysis gasoline cut for a limited amount to the reference gasoline. Our study showed that possibly up to 15 volume % of Sample F can be blended to the refinery gasoline while still meeting the fuels property targets. By integrating the pyrolysis gasoline product with a refinery fuel, the overall product quality can be maintained.

These results indicate that the as-produced gasoline fraction of pyrolysis oil has limited utility as gasoline fuel. Upgrading in a refinery unit is preferred to convert this gasoline fraction of the pyrolysis oil into hydrocarbon that meets the gasoline fuel property targets.

Example 4: Evaluation of Pyrolysis Oil Cut for Jet Fuel

Sample G, a pyrolysis oil cut for jet fuel boiling range, was evaluated to assess its potential to use as jet fuel. Sample G has the carbon number range of C9-C18, typical of the jet fuel.

Due to the olefinic nature of the pyrolysis oil, jet fuel thermal oxidation test (D3241) was considered as the most critical test. The pyrolysis oil jet cut as-is, Sample G, had only 36 minutes of oxidation stability suggesting the pure pyrolysis jet cut is unsuitable for use as jet fuel.

We prepared a 5 volume % blend of pyrolysis jet cut (Sample G) with refinery produced jet. The blend still failed for the jet fuel oxidation test as shown in Table 4.

TABLE 4

Evaluation of Pyrolysis Oil Jet Fraction for Jet Fuel

|  | Jet Fuel Thermal Oxidation Test |
|---|---|
| Reference jet fuel | Passed |
| 5/95 vol. % Blend of Sample G with reference jet fuel | Failed |

These results indicate that the as-produced jet fraction of pyrolysis oil is completely unsuitable for jet fuel, and upgrading in a refinery unit is required to convert this jet fraction of the pyrolysis oil into hydrocarbon that meets the jet fuel property targets.

Example 5: Evaluation of Pyrolysis Oil Cut for Diesel Fuel

Sample H, a pyrolysis oil cut for diesel fuel boiling range, was evaluated to assess its potential to use as diesel fuel. Sample H has the carbon number range of C14-C24, typical of the diesel fuel.

Sample H contains a substantial amount of normal hydrocarbons. Since normal hydrocarbons tends to exhibit waxy characteristics, cold flow properties such as pour point (ASTM D5950-14) and cloud points (ASTM D5773) were considered as the most critical tests.

We prepared two blends at 10 and 20 volume % of Sample H with refinery produced diesel fuel. However, both blends still failed for the target pour point of less than −17.8° C. (0° F.) pour points.

TABLE 5

Evaluation of Pyrolysis Oil Diesel Fraction for Diesel Fuel

|  | Cloud Point (° C.) | Pour Point (° C.) | Pour Point Test |
|---|---|---|---|
| Reference diesel fuel | −17.1 | −19.0 | Passed |
| 10/90 vol. % Blend of Sample H with reference diesel fuel | −11.1 | −12.0 | Failed |
| 20/80 vol. % Blend of Sample H with reference diesel fuel | −5.5 | −7.0 | Failed |

These results indicate that the pyrolysis oil as-is is completely unsuitable for diesel fuel, and upgrading in a refinery unit is required to covert the diesel fraction of pyrolysis oil into hydrocarbon that meets the diesel fuel property targets.

Examples 6: Coprocessing of Pyrolysis Product to FCC Unit or FCC Pretreater Unit Results from Table 1 showed that industrial pyrolysis process of sorted plastics, sourced predominantly from polyethylene and polypropylene waste, produced quality pyrolysis oil or pyrolysis wax made of mostly carbon and hydrogen. With good sorting and efficient pyrolysis unit operation, the nitrogen and sulfur impurities are at low enough levels that a modern refinery can handle cofeeding of pyrolysis feedstocks to their processing units with no detrimental impacts.

However, some pyrolysis oils or wax may still contain high amounts of metals (Ca, Fe, Mg) and other non-metals (N, S, P, Si, Cl, O) that could negatively affect the performance of conversion units in a refinery. For pyrolysis products with high impurity levels are preferentially fed to a FCC feed treater unit before the FCC unit so that bulk of impurities are removed effectively by the pretreater.

By feeding the entire pyrolysis feedstock to a FCC unit as shown in FIG. 2 or to a FCC pretreater unit before the FCC unit, the pyrolysis oil and wax are converted into offgas, LPG paraffins and olefins, FCC gasoline and heavy hydrocarbon components. The FCC gasoline is a valuable gasoline blending component. The heavy fractions, light cycle oil (LCO) and heavy cycle oil (HCO) are converted further in the subsequent conversion units including jet hydrotreating unit, diesel hydrotreating unit, hydrocracking unit and/or coker unit to make more gasoline, jet, and diesel fuel with satisfactory product properties. The LPG paraffins and olefins are either processed further in an alkylation unit, blended in the gasoline poor or in part used for petrochemicals production with a recycle content. The $C_3$ propane and propylene mix steam is a valuable feedstock for polypropylene generation.

The following Examples 7 and 8 demonstrate the conversion of waste plastics pyrolysis product into quality transportation fuel in a refinery conversion unit, using a FCC unit as an example.

Example 7: Conversion of Pyrolysis Oil in FCC

To study the impact of coprocessing of waste plastics pyrolysis oil to FCC, series of laboratory tests were carried out with Samples A and C. Vacuum gas oil (VGO) is the typical feed for FCC. FCC performances of 20 volume % blend of pyrolysis oil with VGO and pure pyrolysis oil were compared with that of the pure VGO feed.

The FCC experiments were carried out on a Model C ACE (advanced cracking evaluation) unit fabricated by Kayser Technology Inc. using regenerated equilibrium catalyst (Ecat) from a refinery. The reactor was a fixed fluidized reactor using $N_2$ as fluidization gas. Catalytic cracking experiments were carried out at the atmospheric pressure and 900° F. reactor temperature. The cat/oil ratio was varied between 5 to 8 by varying the amount of the catalyst. A gas product was collected and analyzed using a refinery gas analyzer (RGA), equipped with GC with FID detector. In-situ regeneration of a spent catalyst was carried out in the presence of air at 1300° F., and the regeneration flue gas was passed through a LECO unit to determine the coke yield. A liquid product was weighted and analyzed in a GC for simulated distillation (D2887) and $C_5^-$ composition analysis. With a material balance, the yields of coke, dry gas components, LPG components, gasoline (C5-430° F.), light cycle oil (LCO, 430-650° F.) and heavy cycle oil (HCO, 650° F.$^+$) were determined. The results are summarized below in Table 6.

TABLE 6

Evaluation of Pyrolysis Oil Cofeeding to FCC

| Feed | 100% VGO | 20/80 vol % blend, Sample A/VGO | 20/80 vol % blend, Sample C/VGO | 100% Sample A | 100% Sample C |
|---|---|---|---|---|---|
| Cat/Oil, wt/wt | 6.0 | 6.0 | 6.0 | 6.0 | 6.0 |
| Conversion, wt %* | 81.3 | 83.15 | 83.09 | 76.1 | 78.82 |
| WLP Impurity** | | | | | |
| Total O, ppm | 81 | 76 | 62 | 54 | 67 |
| Total N, ppm | 27 | 30 | 33 | 50 | 21 |
| Yields | | | | | |
| Coke, wt % | 4.45 | 4.35 | 4.20 | 3.56 | 2.90 |
| Total Dry Gas, wt % | 2.08 | 1.96 | 1.93 | 1.55 | 1.43 |
| Hydrogen | 0.16 | 0.12 | 0.12 | 0.05 | 0.04 |
| Methane | 0.68 | 0.65 | 0.64 | 0.50 | 0.46 |
| Ethane | 0.44 | 0.43 | 0.41 | 0.33 | 0.28 |
| Ethylene | 0.76 | 0.74 | 0.72 | 0.63 | 0.61 |
| Total LPG, wt % | 21.25 | 21.08 | 21.50 | 20.17 | 24.40 |
| Propane | 1.78 | 1.76 | 1.72 | 1.47 | 1.53 |
| Propylene | 5.53 | 5.51 | 5.56 | 5.57 | 6.75 |
| n-Butane | 1.56 | 1.56 | 1.54 | 1.29 | 1.34 |
| Isobutane | 6.61 | 6.48 | 6.64 | 5.43 | 6.61 |
| C4 olefins | 5.77 | 5.77 | 6.04 | 6.41 | 8.16 |
| Gasoline, wt % | 53.53 | 55.75 | 55.46 | 62.53 | 61.75 |
| LCO, wt % | 12.89 | 12.23 | 11.93 | 10.37 | 8.03 |
| HCO, wt % | 5.81 | 4.63 | 4.98 | 1.82 | 1.50 |
| Octane Number*** | 88.05 | 84.57 | 82.79 | 73.75 | 75.41 |

*Conversion – conversion of 430° F.$^+$ fraction to 430° F.$^-$
**Impurity level of N and O in whole liquid product in fuels boiling range by GC x GC, ppm
***Octane number, (R + M)/2, was estimated from detailed hydrocarbon GC of FCC gasoline.

The results in Table 6 show that up to 20 volume % cofeeding of pyrolysis oil only makes very slight changes in the FCC unit performance indicating coprocessing of pyrolysis oil up to 20% is readily feasible. The 20 volume % blending of Sample A or Sample C led to very slight reduction of coke and dry gas yields, slight increase in gasoline yield and slight decrease in LCO and HCO, which are favorable in most situations. With paraffinic nature of pyrolysis oil, the 20% blends of A and C lowered the Octane number by about 3-5 numbers. With refinery operational flexibility, these octane number debits can be compensated with blending or feeding location adjustments.

The FCC unit cracks the pyrolysis oil info fuel range hydrocarbons, reduces impurities, and isomerize n-paraffins to isoparaffins. All these chemistry will improve the fuel properties of the pyrolysis oil and wax. By cofeeding the pyrolysis oil through the FCC process unit with a zeolite catalyst, the oxygen and nitrogen impurities in the fuel range were reduced substantially, from about 300-1400 ppm N to about 30 ppm N and from about 250-540 ppm O to about 60-80 ppm O. The hydrocarbon composition of all these cofeeding products are well within the typical FCC gasoline range.

The FCC runs of 100% pyrolysis oil showed substantial debits of Octane numbers by about 13-14 numbers. This shows that coprocessing of pyrolysis oil is preferred over processing of pure 100% pyrolysis oil.

Example 8: Feeding of Recycled $C_3$ for Propylene Isolation or Production, Followed by Productions of Polypropylene Resin and Polypropylene Consumer Products The pyrolysis oil cofeeding to a FCC unit, as shown in Example 7 produces a substantial amount of $C_3$ LPG steam with a recycle content. The $C_3$ stream is a good feedstock to feed to a polymerization unit for production of polypropylene polymer with a recycle content. To achieve this, the $C_3$ LPG stream containing propane and propylene is captured and fed to a propane/propylene (P/P) splitter to isolate a pure propylene steam (>99 mol %), which is then fed to a propylene polymerization unit. The propane from the P/P splitter may be dehydrogenated to produce additional propylene for the polymerization unit.

The polypropylene resin containing some recycled-polyethylene/polypropylene derived materials has high quality that is indistinguishable to that of the virgin polypropylene resin made entirely from virgin petroleum resources. The polypropylene resin with the recycled material is then further processed to produce various polypropylene products to fit the needs of consumer products. These polypropylene consumer products now contain chemically recycled, circular polymer while qualities of the polypropylene consumer products are indistinguishable from those made entirely from virgin polypropylene polymer. These chemically recycled polymer products are different from the mechanically recycled polymer products whose qualities are inferior to the polymer products made from virgin polymers.

Examples 9: Coprocessing of Pyrolysis Wax to Isomerization Dewaxing Unit to Produce Lubricating Base Oil Results from Table 1 showed that industrial pyrolysis process of sorted plastics, sourced predominantly from polyethylene and polypropylene waste, produced pyrolysis wax made of mostly carbon and hydrogen. Various process options were examined for making lubricating base oil from the pyrolysis wax via hydroisomerization dewaxing process.

The pyrolysis wax still contain too high amounts of nitrogen and sulfur impurities, metals (Ca, Fe, Mg) and other non-metals (P, Si, Cl, O) that negatively affect the performance of the hydroisomerization dewaxing catalyst containing precious metal (Pt, Pd, or a combination of Pt and Pd) and a zeolite such as ZSM-11, ZSM-23, ZSM-48, SSZ-32, SSZ-91, SAPO-11, SAPO-31 and SAPO-41.

An attempt to make quality lubricating base oil by direct feeding of pure pyrolysis oil using a dewaxing catalyst was not successful, as shown below in Example 10. To maintain the catalyst activity, for direct feeding of pyrolysis wax to the hydroisomerization dewaxing unit, the cofeeding level needs to be limited less than 10 vol. %, preferentially less than 5 vol. %. The volume percent limitation is likely coming from the nitrogen impurity which is detrimental to the zeolite activity. The nitrogen level of the combined feed needs to be maintained at less than 5 ppm nitrogen, preferentially less than 1 ppm nitrogen.

Alternatively, the pyrolysis wax is cofed to a hydrocracking unit to remove S, N, and other impurities. The hydrocracking unit hydrogenates the pyrolysis wax and removes impurities. The hydrocracking unit severity may be adjusted to maximize the base oil yield of the combined feed. Cofeeding level to the hydrocracking unit can be as much as 50 vol. %, preferentially 20 vol. %. In this case, the volume percent limitation may come from the metals impurity or N impurity or P impurity depending on the unit configuration and the catalyst choice. The bottom fraction (650° F.+) containing hydrocracked pyrolysis wax is then fed to the hydroisomerization dewaxing unit to make a lubricating base oil.

Alternatively, the pyrolysis wax is fed to a dedicated hydrogenation unit to remove S, N, and other impurities before fed to the hydroisomerization dewaxing unit to make a base oil. The hydrogenation step removes impurities very easily, as shown in Example 11 below. The hydrotreated wax can be cofed to the hydroisomerization dewaxing at any volume percent.

The following Examples 10 and 11 demonstrate an unsuccessful route and a successful process route of making quality base oil in refinery conversion units using waste plastics pyrolysis wax as the feedstock.

Example 10: Production of Base Oil from Recycled Pyrolysis Wax Via Hydroisomerization Dewaxing Process Only To assess the potential of base oil production from the recycled wax, Sample E, crude pyrolysis wax, was vacuum distilled to produce 690° F.+ fraction, Sample J. 100% Sample J was hydroisomerized in a batch autoclave unit with a Pt/SSZ-32/Alumina catalyst overnight at an oil to catalyst weight ratio of 10:1, at 650° F. and under 800 psig $H_2$ pressure. The hydrogenated product was vacuum distilled to produce 690° F.+ boiling and clear oil, Sample K. Properties of the samples are summarized in Table

TABLE 7

Dewaxing of Pyrolysis Wax with Pt/Zeolite Catalyst

| Description | Sample E | Sample J, Slack Wax | Sample K, Dewaxed oil |
|---|---|---|---|
| | As-received pyrolysis wax | 690° F.+ wax cut of Sample E | 690° F.+ oil from dewaxing of Sample J followed by distillation |
| Simulated Distillation, ° F. | | | |
| 0.5% (Initial Boiling Point) | 325 | 680 | 694 |
| 5% | 475 | 715 | 727 |
| 10% | 545 | 727 | 742 |
| 30% | 656 | 768 | 783 |
| 50% | 733 | 807 | 820 |
| 70% | 798 | 854 | 865 |
| 90% | 894 | 930 | 939 |
| 95% | 939 | 970 | 980 |
| 99.5% (Final Boiling Point) | 1064 | 1067 | 1096 |
| Bromine Number, g/100 g | 14 | 6 | <0.1 |
| Contaminants | | | |
| Total S, ppm | 6.3 | — | — |
| Total N, ppm | 237 | 180 | <0.3 |
| Total Cl, ppm | 4.7 | 1.9 | — |
| Trace Elemental Impurities | | | |
| Fe, ppm | 3.1 | 3.0 | <1.1 |
| P, ppm | 20.2 | 32.5 | <0.55 |
| Si, ppm | 3.1 | <2.7 | <2.2 |
| Color & physical state | Light brown solid | Light brown solid | Clear liquid |
| Viscosity Index (VI) | — | 169 | 162 |
| Viscosity at 100° C., cSt | — | 4.26 | 4.67 |
| Viscosity at 70° C., cSt | — | 7.52 | — |
| Viscosity at 40° C., cSt | — | — | 19.81 |
| Pour Point, ° C. | 42 | — | 12 |
| Cloud Point, ° C. | — | — | 20 |

Sample J, 690° F.+ cut slack wax from waste plastic pyrolysis, is low-viscosity wax at ~4.3 cSt at 100° C. with an excellent viscosity index of 169. However, the slack wax contains significant amounts of N (180 ppm) and P (32.5 ppm) which will passivate the zeolite catalyst activity in the hydroisomerization dewaxing process. Sample K, dewaxed and distilled oil, showed viscosity index of 162 and the pour point of 12° C. Even though the pour point was reduced substantially from 42° C. of Sample E, the pour point of 12° C. is still very poor relative to the industry target of −15° C. or below. This oil cannot be used for high performance modern lubricant as this oil will lose fluid/oily characters when the ambient temperature drops below 12° C. and the oil will become thick or solid-like material.

This study indicates that pyrolysis wax needs to be hydrotreated or hydrocracked to reduce the N impurity and other impurities in order to produce an acceptable base oil from a waste plastics pyrolysis wax.

Example 11: Production of Quality Base Oil with Recycle Content by Hydrotreating Followed by Hydroisomerization Dewaxing Process Sample E, crude pyrolysis wax, was hydrogenated in a continuous fixed bed unit containing a NiMo/Alumina catalyst at 625° F. reactor temperature and 1200 psig pressure. A liquid feed flow rate of 1.5 hr$^{-1}$ relative to the catalyst bed volume and H$_2$/Hydrocarbon flow rate of 2500 scf/bbl were used to produce the hydrogenated product, which is mostly wax. The hydrogenated product was vacuum distilled to produce 650° F.$^+$ fraction as a hydrogenated pyrolysis paraffin wax, Sample L.

Sample L, hydrogenated wax made from waste plastics pyrolysis, was subjected to hydroisomerization dewaxing in a continuous fixed bed unit containing a Pt/ZZS-91/Alumina catalyst at 625° F. reactor temperature and 400 psig pressure. A liquid feed flow rate of 1.0 hr$^{-1}$ relative to the catalyst bed volume and H$_2$/Hydrocarbon flow rate of 2500 scf/bbl were used to produce the dewaxed oil. The dewaxed oil was vacuum distilled to produce 690° F.$^+$ fraction as the final dewaxed base oil product, Sample M. The results are summarized in Table 8.

TABLE 8

Hydrotreating/Dewaxing of Pyrolysis Wax for Lubricating Base Oil Production

| | Sample E | Sample L, Hydrogenated Wax | Sample M, Dewaxed oil |
|---|---|---|---|
| Description | As-received pyrolysis wax | Hydrogenated Sample E, cut at 650° F.$^+$ | Dewaxed Sample L, cut at 690° F.$^+$ |
| Simulated Distillation, ° F. | | | |
| 0.5% (Initial Boiling Point) | 325 | 625 | 651 |
| 5% | 475 | 671 | 681 |
| 10% | 545 | 686 | 695 |
| 30% | 656 | 735 | 738 |
| 50% | 733 | 781 | 782 |
| 70% | 798 | 834 | 836 |
| 90% | 894 | 917 | 923 |
| 95% | 939 | 958 | 965 |
| 99% (Final Boiling Point) | 1033 | 1041 | 1048 |
| Bromine Number, g/100 g | 14 | <0.09 | — |
| Contaminants | | | |
| Total S, ppm | 6.3 | Below detection | — |
| Total N, ppm | 237 | <0.4 | — |
| Total Cl, ppm | 4.7 | Below detection | — |
| Trace Elemental Impurities | | | |
| Fe, ppm | 3.1 | <1.1 | — |
| P, ppm | 20.2 | <2.2 | — |
| Si, ppm | 3.1 | <2.7 | — |
| Color & physical state | Light brown solid | White solid | Clear liquid |
| Viscosity Index | — | 163 | 135 |
| Viscosity at 100° C., cSt | — | 3.80 | 4.05 |
| Viscosity at 70° C., cSt | — | 6.66 | — |
| Viscosity at 40° C., cSt | — | — | 17.39 |
| Pour Point, ° C. | 42 | 51 | −35 |
| Cloud Point, ° C. | — | — | −17 |

Hydrogenation of pyrolysis wax, Sample E, produced excellent quality hydrogenated wax, Sample L. All trace impurities are completely removed upon hydrogenation in that Sample L has no measurable impurities that could harm the dewaxing catalyst. This example shows that high quality, pure paraffinic wax can be produced effectively from waste plastic containing predominately polyethylene, polypropylene and that mild hydrogenation is a very effective method to purify the waste plastic derived wax.

Hydroisomerization dewaxing of the hydrogenated wax (Sample L) produced remarkably excellent quality 4 cSt base oil with viscosity index of 135, pour point of −35° C. and cloud point of −17° C. (Sample M). In terms of the quality, this base oil made from waste plastics pyrolysis falls in the Group III base oil category. These positive results were quite surprising considering the poor property observed with Sample K. Low viscosity 4 cSt base oil is highly desirable as it is widely used as a component in automotive lubricants.

The Examples 10 and 11 clearly showed that excellent quality base oil can be made from the wax derived from pyrolysis of polyethylene and polypropylene waste with careful selection of cofeeding process configuration and process conditions. The results clearly show that the preferred way to make a base oil from a waste plastics pyrolysis wax is by hydrogenation followed by hydroisomerization dewaxing process. The final base oil produced has a recycle content, and the quality of the base oil is comparable or superior to that of base oil produced by the conventional refinery processing with virgin crude oil.

The foregoing examples together clearly show a new effective way to recycle a large quantity of polyethylene and polypropylene derived waste plastics via chemical recycling through pyrolysis followed by cofeeding of the pyrolysis products in a refinery via efficient integration. This integration allows quality fuels, lubricating base oil and circular polymer productions.

As used in this disclosure the word "comprises" or "comprising" is intended as an open-ended transition meaning the inclusion of the named elements, but not necessarily excluding other unnamed elements. The phrase "consists essentially of" or "consisting essentially of" is intended to mean the exclusion of other elements of any essential significance to the composition. The phrase "consisting of" or "consists of" is intended as a transition meaning the exclusion of all but the recited elements with the exception of only minor traces of impurities.

All patents and publications referenced herein are hereby incorporated by reference to the extent not inconsistent herewith. It will be understood that certain of the above-described structures, functions, and operations of the above-described embodiments are not necessary to practice the present invention and are included in the description simply for completeness of an exemplary embodiment or embodiments. In addition, it will be understood that specific structures, functions, and operations set forth in the above-described referenced patents and publications can be practiced in conjunction with the present invention, but they are not essential to its practice. It is therefore to be understood that the invention may be practiced otherwise that as specifically described without actually departing from the spirit and scope of the present invention as defined by the appended claims.

What is claimed is:

1. A continuous process for converting waste plastic into recycle for polypropylene polymerization comprising:
   (a) selecting waste plastics containing polyethylene and/or polypropylene wherein the selected plastics contain less than 5 wt % polyethylene terephthalate and polyvinyl chloride;
   (b) passing the waste plastics from (a) through a pyrolysis reactor to thermally crack at least a portion of the waste plastics and produce a pyrolyzed effluent;
   (c) separating the pyrolyzed effluent into offgas, a naphtha/diesel fraction, a heavy fraction, and char;
   (d) passing the naphtha/diesel fraction to a refinery FCC unit along with virgin crude oil with volume flow of the naphtha/diesel fraction comprising about 50 volume % or less of total hydrocarbon flow to the FCC unit;

(e) recovering a liquid petroleum gas $C_3$ olefin/paraffin mixture from the FCC unit;

(f) separating the $C_3$ paraffin and $C_3$ olefin into different fractions;

(g) passing the $C_3$ paraffin to a dehydrogenation unit to produce $C_3$ olefin;

(h) passing $C_3$ olefin to a propylene polymerization reactor;

(i) passing the heavy fraction to an isomerization dewaxing unit to produce a base oil; and (j) recovering a gasoline and heavy fraction from the FCC unit and further processing in the refinery to gasoline.

2. The process of claim 1, wherein polypropylene is produced in the propylene polymerization reactor of (h).

3. The process of claim 1, wherein the naphtha/diesel fraction of (d) is passed directly to a refinery FCC unit distillation section.

4. The process of claim 1, wherein the waste plastics selected in (a) are from the plastics classification groups 2, 4, and/or 5.

5. The process of claim 1, wherein a heavy fraction is recovered from the FCC unit distillation column and further processed in the refinery to diesel or jet fuel.

6. The process of claim 1, wherein gasoline and heavy fractions are produced by the FCC unit, with the amounts being increased due to the naphtha/diesel fraction passed to the FCC unit.

7. The process of claim 1, wherein the amount of base oil produced by the isomerization dewaxing unit is increased due to the naphtha/diesel fraction passed to the FCC unit.

8. The process of claim 1, wherein the heavy fraction in (i) is hydrotreated and then isomerized in the dewaxing unit.

9. The process of claim 1, wherein the naphtha/diesel flow to the FCC unit comprises up to about 20 volume % of the total hydrocarbon flow to the FCC unit.

10. A process for converting waste plastic to chemicals useful in preparing polypropylene and lubricating oil comprising:

(a) selecting waste plastics containing polyethylene and/or polypropylene wherein the selected plastics contain less than 5 wt % polyethylene terephthalate and polyvinyl chloride;

(b) pyrolyzing the waste plastic and recovering a naphtha/diesel fraction and a heavy fraction;

(c) passing the naphtha/diesel fraction to a refinery FCC unit along with virgin crude oil with volume flow of the naphtha/diesel fraction comprising about 50 volume % or less of total hydrocarbon flow to the FCC unit; and (d) passing the heavy fraction to an isomerization dewaxing unit.

\* \* \* \* \*